(12) United States Patent
Mortensen

(10) Patent No.: US 8,318,218 B2
(45) Date of Patent: Nov. 27, 2012

(54) COMPOSITION COMPRISING 1,3/1, 6 BETA GLUCAN FOR REDUCING WEIGHT

(75) Inventor: Nils Chr. Mortensen, Tonsberg (NO)

(73) Assignee: Medeq AS, Tonsberg (NO)

( * ) Notice: Subject to any disclaimer, the term of this patent is extended or adjusted under 35 U.S.C. 154(b) by 57 days.

(21) Appl. No.: 12/995,081

(22) PCT Filed: May 29, 2009

(86) PCT No.: PCT/GB2009/001351
§ 371 (c)(1),
(2), (4) Date: Feb. 18, 2011

(87) PCT Pub. No.: WO2009/144467
PCT Pub. Date: Dec. 3, 2009

(65) Prior Publication Data
US 2011/0135762 A1    Jun. 9, 2011

(30) Foreign Application Priority Data
May 29, 2008    (GB) .................................. 0809808.9

(51) Int. Cl.
*A01N 65/00*    (2009.01)

(52) U.S. Cl. ...................................................... 424/725

(58) Field of Classification Search .................. None
See application file for complete search history.

(56) References Cited

U.S. PATENT DOCUMENTS
2002/0102316 A1    8/2002    Weissman

FOREIGN PATENT DOCUMENTS

| EP | 10 64 858 | 1/2003 |
| EP | 1 987 812 | 11/2008 |
| JP | 11-225706 | 8/1999 |
| JP | 2004-129518 | 4/2004 |
| JP | 2008-214273 | 9/2008 |
| KR | 10-2004-0008291 | 1/2004 |
| KR | 10-0623210 | 9/2006 |
| WO | WO 2007/035007 | 3/2007 |
| WO | WO 2008/051862 | 5/2008 |

OTHER PUBLICATIONS

International Search Report for PCT/GB2009/001351, mailed Aug. 6, 2009.
Written Opinion of the International Searching Authority for PCT/GB2009/001351, mailed Aug. 6, 2009.
UK Search Report for GB No. 0809808.9, dated Sep. 29, 2008.
Zhang, B. et al., "The modulating effect of bet-1,3/1,6-Glucan Supplementation in the Diet on Performance and Immunological Responses of Broiler Chickens", Asian-Australian Journal of Animal Sciences, vol. 21, No. 2, (Feb. 1, 2008), pp. 237-244.
Goyal, R,K. et al., "Beneficial Effects of Zingiber Officinate on Goldthioglucose Induced Obesity", Fitoterapia, vol. 77, No. 3, (Apr. 1, 2006), pp. 160-163.
Galisteo, MI et al., "A Diet Supplemented with Husks of Plantago Ovata Reduces the Development of Endothelial Dysfunction, Hypertension, and Obesity by Affecting Adiponectin and TNF-Alpha in Obese Zucker Rats", The Journal of Nutrition, vol. 135, No. 10, (Oct. 2005), pp. 2399-2404.
Aoki, F. et al., "Suppression by Licorice Flavonoids of Abdominal Fat Accumulation and Body Weight Gain in High-Fat Diet-Induced Obese C57BL/6J Mice", Bioscience, Biotechnology and Biochemistry, vol. 71, No. 1, (Jan. 2007), pp. 206-214.
Rack-Kotilla, E. et al., "The Action of Tarazacum Officinale Extracts on the Body Weight and Diuresis of Laboratory Animals", Planta Medica, vol. 26, No. 3, (Nov. 1, 1974), pp. 212-217.

*Primary Examiner* — Michael Meller
(74) *Attorney, Agent, or Firm* — Nixon & Vanderhye P.C.

(57) ABSTRACT

Beta-1,3/1,6-glucan for use as a slimming aid or in weight loss or for the treatment of obesity.

2 Claims, No Drawings

COMPOSITION COMPRISING 1,3/1, 6 BETA GLUCAN FOR REDUCING WEIGHT

This application is the U.S. national phase of International Application No. PCT/GB2009/001351 filed 29 May 2009, which designated the U.S. and claims priority to GB Application No. 0809808.9 filed 29 May 2008, the entire contents of each of which are hereby incorporated by reference.

This invention relates to the use of 1,3/1,6 beta glucans in the treatment of obesity or for the cosmetic control of weight. In particular, the invention provides an oral dosage form to encourage weight loss.

Metabolic syndrome has recently been recognized as a public health concern. This is operationally defined as the presence of any three of the following factors:
central obesity (high waist circumference), hyperglycemia, high blood pressure, low high-density lipoprotein cholesterol (HDL-C) or high triglycerides.

While metabolic syndrome alone is a disabling condition, it is also an intermediary step in the progression of a number of vascular and coronary-related clinical events. Observational evidence suggests that central obesity is a key element of metabolic syndrome, and recent studies suggest an etiologic role for visceral adipose tissue.

For several years it has been known that a waist line circumference of ≧80 cm in females and ≧94 cm in males may be used as a clinical cardiovascular risk assessment in interpretation of health risks. Even though extensive resources have been used in the research and treatment of obesity during the last decades however, the results have been disappointing, according to reports from WHO. There has been no reduction in the epidemic of excess weight and obesity by means of the current and historical approaches to the problem. Thus, alternative methods must be developed.

Obesity is generally considered to be the end result of long standing positive energy balance. However, some alternative possibilities for the etiology of obesity have been discussed.

The possibility that obesity may be associated with viral infections has been mooted in some circles (Vasilakopoulou A, le Roux C W. "Could a virus contribute to weight gain?" Int J Obesity 2007; 31:1350-1356). Environmental, genetic, neural and endocrine factors may also contribute to its development. The rapid global spread of obesity resembles epidemiologically the spread of an infectious disease Surprisingly, little consideration has been given to the possibility that the epidemic of obesity could be due to an infectious agent, however.

In animals, seven viruses and a scrape agent have been shown to cause obesity, and adenoviruses Ad-31 and Ad-9 have been shown to be radiogenic in animal cell cultures (Schilder R J, Marden J H. "Metabolic syndrome and obesity in an insect." PNAS 2006; 103: 18805-18809. Schilder R J, Marden J H. "Parasites, proteomics and performance: effects of gregarine gut parasites on dragonfly flight muscle composition and function." J Exp Biol 2007; 210:4298-4306.). In humans, small EDRK-rich factor 1A (SMAM-1) has also been implicated in obesity. The search for suitable agents to treat such infections is underway.

From the literature there is also evidence to indicate that the body's natural weight-control mechanisms are not functioning properly in obesity. Because the obesity epidemic occurred relatively quickly it has been suggested that environmental causes instead of genetic factors may be largely responsible for this. The Earth's environment and its usage has changed significantly during the last decades because of the exponential production and usage of synthetic organic and inorganic chemicals. Many of these chemicals are better know for causing weight loss at high levels of exposure but much lower concentrations of these chemicals have powerful weight-promoting actions.

This property has already been widely exploited commercially to produce growth hormones that fatten livestock, and pharmaceuticals that induce weight gain in grossly underweight patients. One hypothesis is that the current level of human exposure to these chemicals may have damaged many of the body's natural weight-control mechanisms. It might be that these exposures have damaged many of the body's natural weight-control mechanisms. These effects, together with a wide range of additional, possibly synergistic factors, may play a significant role in the worldwide obesity epidemic (Balille-Hamilton P F. "Chemical toxins: a hypothesis to explain the global obesity epidemic." J Altern Complement Med 2002; 8:185-192).

Obesity is also known to create low-grade Systemic Inflammatory Response Syndrome (SIRS) that is similar (but on a smaller scale) to gram-negative sepsis. This process involves up-regulation of systemic immunity, is characterized clinically by insulin resistance and metabolic syndrome, and puts the subject at increased risk for organ failure, infectious morbidity and mortality.

Through lipotoxicity and cytokine dysregulation, obesity may act to prime the immune system, and predispose the subject to an exaggerated subsequent immune response when a second clinical insult occurs (such as trauma, burns, or myocardial infarction).

Clinical evidence suggests that fat cells (adipocytes) once thought to be metabolically inert may represent dynamic sources of pro-inflammatory, metabolically active substances such as cytokines and reflect a potent dysregulation of the delicate metabolic homeostasis.

Abnormal production of tumour necrosis factor alpha, various interleukins, leptin and numerous other inflammatory mediators lead to insulin resistance, increased blood pressure and subsequent development of secondary illnesses. Many of these secondary illnesses associated with obesity may reflect increased macrophage infiltration in adipose tissue. Macrophage infiltration is a classic inflammatory response.

Not only therefore can the targeting of obesity cause a general health benefit in terms of mobility, appearance and so on but it can also be critical in preventing various consequential conditions.

Specialized nutrition therapy for such patients currently consist of a hypocaloric, high protein diet. However, this approach does not address the putative pathophysiological mechanisms of inflammation and altered metabolism associated with obesity.

There remains therefore a need to devise new treatments for obesity bearing in mind that cause of the obesity epidemic may well be more complex than simply over eating and lack of exercise.

Beta-Glucans have been studied for over twenty years for their favourable biological effects in mammals. It is common knowledge in the scientific community that Beta-Glucan is a powerful immunostimulant and a very powerful antagonist to both benign and malignant tumors. It lowers cholesterol and triglyceride levels, normalizes blood sugar level and heals and rejuvenates the skin (Akramiene D, Kondrotas A, Didziapetriene J, Kevelaitis E. "Effects of β-glucans on the immune system." Medicina (Kaunas) 2007; 43: 597-606.).

By recognizing the role of toxins in obesity and altered function of the neuroendocrine-immune and the mitochondrial and redox systems, and by creating a comprehensive strategy for both reduction of exposure to and elimination of toxins, as well as the development of effective clinical strategies, treatment resistance to obesity may be more successfully addressed.

The present inventors have developed a composition to significantly and safely reduce body weight, body fat and body mass index as well as waist, abdominal, and hip circumferences. The preparation also has beneficial effects in preventing metabolic syndrome. The present inventors use beta-1,3/1,6 glucans to encourage weight loss in a patient and it is believed that no-one before has employed this specific glucan in such a weight loss composition. There are many forms of beta-glucans but it is only beta-1,3/1,6 glucans which the inventors have shown to be remarkably effective in encouraging weight loss.

Thus, viewed from a first aspect the invention provides at least one beta-1,3/1,6-glucan for use as a slimming aid or in weight loss or for the treatment of obesity.

Viewed from another aspect the invention provides a composition comprising at least one beta-1,3/1,6-Glucan and at least one plant extract selected from the group consisting of an extract from the genus *silybum* (e.g. blessed milk thistle (*Silybum marianum*)), an extract from golden root (*Rhodiola Rosea*), a plant extract from the genus *Cynara*, e.g. global artichoke (*Cynara scolymus*), a plant extract from the genus *Schisandra* e.g. (*Schisandra chinensis*), a plant extract from the genus *Glycyrrhiza*, e.g. licorice root (*Glycyrrhiza glabra*), a plant extract from the genus *taraxacum* (dandelion), a burdock seed extract (*Arctium lappa*), a burdock root extract (*Arctium lappa*), a ginger extract (*Zingiber officinalis*), a dong quai extract (e.g. root of *Angelica sinensis*), a plantain seed extract (*Plantago major*), and plantain plant extract (*Plantago major*).

Viewed from another aspect the invention provides a composition comprising at least one beta-1,3/1,6-Glucan and optionally at least one plant extract selected from the group consisting of an extract from the genus *silybum* (e.g. blessed milk thistle (*Silybum marianum*)), an extract from golden root (*Rhodiola Rosea*), a plant extract from the genus *Cynara*, e.g. global artichoke (*Cynara scolymus*), a plant extract from the genus *Schisandra* e.g. (*Schisandra chinensis*), a plant extract from the genus *Glycyrrhiza*, e.g. licorice root (*Glycyrrhiza glabra*), a plant extract from the genus *taraxacum* (dandelion), a burdock seed extract (*Arctium lappa*), a burdock root extract (*Arctium lappa*), a ginger extract (Zingiber officinalis), a dong quai extract (e.g. root of *Angelica sinensis*), a plantain seed extract (*Plantago major*), and a plantain plant extract (*Plantago major*) for use as a slimming aid or in weight loss or for the treatment of obesity.

Viewed from a still further aspect the invention provides beta-1,3/1,6-glucan or a composition comprising at least one beta-1,3/1,6-glucan and optionally at least one plant extract selected from the group consisting of an extract from the genus *silybum* (e.g. blessed milk thistle (*Silybum marianum*)), an extract from golden root (*Rhodiola Rosea*), a plant extract from the genus *Cynara*, e.g. global artichoke (*Cynara scolymus*), a plant extract from the genus *Schisandra* e.g. (*Schisandra chinensis*), a plant extract from the genus *Glycyrrhiza*, e.g. licorice root (*Glycyrrhiza glabra*), a plant extract from the genus *taraxacum* (dandelion), a burdock seed extract (*Arctium lappa*), a burdock root extract (*Arctium lappa*), a ginger extract (*Zingiber officinalis*), a dong quai extract (e.g. root of *Angelica sinensis*), a plantain seed extract (*Plantago major*), and a plantain plant extract (*Plantago major*) for use in the treatment of metabolic syndrome (Systemic Inflammatory Response Syndrome (SIRS)).

In a further aspect, the invention provides a method of treatment of clinical obesity comprising administration of the composition as hereinbefore defined.

The composition may also be used for cosmetic purposes, i.e. to induce weight loss in those overweight as opposed to clinically obese. Thus, viewed from a further aspect the invention provides a method of losing weight in a patient having a body mass index of less than 30 comprising administration of the composition as herein before defined.

The invention further provides a food supplement comprising the composition of the invention. The composition of the invention might also form part of a beverage.

The compositions of the invention comprise beta 1,3/1,6 glucans. Beta glucans are polysaccharides that only contain glucose as structural components. Beta 1,3-D glucans are chains of D-glucose molecules, with the six-sided D-glucose rings connected at the 1 and 3 positions. The form of Beta 1,3-D glucan used in this invention are those that also contain a number of 1,6 linkages in the longer beta-1,3 glucan backbone. These are referred to as beta-1,3/1,6 glucans and are well known organic compounds.

One of the most common sources of Beta 1,3/1,6 glucans is from the cell wall of baker's yeast (*Saccharomyces cerevisiae*). The beta 1,3/1,6-D glucans from yeast are often insoluble. Other sources of beta-1,3/1,6 glucans include some types of seaweed and various species of mushrooms such as Reishi, Shiitake, and Maitake.

The beta-1,3/1,6 glucans of the invention are preferably derived from *Saccharomyces cerevisia*. Ideally, the beta-1,3/1,6 glucans of the invention are water insoluble. These glucans are available from known commercial sources.

The amount of glucan in the compositions of the invention can vary depending on the number of dosage forms which the patient is to take. Conveniently, a patient should consume around 100 to 2000 mg, e.g. 250 to 1000 mg of glucan per day, preferably 300 to 750 mg, especially 400 to 600 mg, e.g. 500 mg.

This can be achieved in a single dosage form taken once a day or preferably in multiple dosage forms. Ideally, dosage forms should be taken with meals, i.e. 3 times a day or morning and night. Each dosage form of the invention may therefore contain half, a third or a quarter, for example of the daily amounts proposed above, e.g. 50 to 200 mg, especially 100 to 150 mg.

As well as glucans, the compositions of the invention can comprise at least one plant extract selected from the group consisting of an extract from the genus *silybum* (e.g. blessed milk thistle (*Silybum marianum*)), an extract from golden root (*Rhodiola Rosea*), a plant extract from the genus *Cynara*, e.g. global artichoke (*Cynara scolymus*), a plant extract from the genus *Schisandra* e.g. (*Schisandra chinensis*), a plant extract from the genus *Glycyrrhiza*, e.g. licorice root (*Glycyrrhiza glabra*) and a plant extract from the genus *taraxacum* (dandelion). In addition or alternatively, the compositions of the invention may contain at least one extract selected from a plant extract from the genus *taraxacum* (dandelion), a burdock seed extract (*Arctium lappa*), a burdock root extract (*Arctium lappa*), a ginger extract (*Zingiber officinalis*), a dong quai extract (e.g. root of *Angelica sinensis*), a plantain seed extract (*Plantago major*), and a plantain plant extract (*Plantago major*).

Preferably, the composition of the invention will contain a plant extract from the genus *silybum*. Preferred species include *Silybum eburneum* (known as the silver milk thistle, elephant thistle and especially *S. marianum*. This plant is believed to enhance bowel function and therefore acts in the composition of the invention to alleviate the symptoms of constipation. Constipation is often associated with individuals who are obese. In particular, this herb improves digestion and energy levels.

The compositions of the invention also preferably contain *Rhodiola Rosea*, This well known plant is used to improve mood and resist depression. Patients with obesity can often finds themselves depressed by their condition making treatment therefore even more difficult as many of these individuals turn to food or alcohol during bouts of depression. The combination therefore of the beta glucans and *Rhodiola Rosea* is ideal as not only is the patient experiencing weight loss but is also taking a mood enhancer making them more likely to take their medication and making them feel positive about their attempts to loose weight.

A further preferred component of the invention is a plant extract from the genus *Cynara*, especially *Cynara scolymus*. Other potential extracts derive from *Cynara cardunculus* and *Cynara humilis*. This extracts are believed to enhance bile function and hence liver function in general.

A further preferred component of the invention is a plant extract from the genus *Schisandra* e.g. (*Schisandra chinensis*). These extracts maintain healthy liver function and may prevent irritable bowel syndrome. In particular, this herb improves digestion and energy levels.

A further preferred component of the invention is a plant extract from the genus *Glycyrrhiza*, e.g. licorice root (*Glycyrrhiza glabra*). Licorice has a broad range of medicinal benefits and also acts as a sweetener making it an ideal component of the present formulation. In particular, this herb improves digestion and energy levels.

A further preferred component of the invention is a plant extract from the genus *taraxacum* (dandelion). Dandelion extracts are high in vitamin A, vitamin C, calcium and iron and they act both as a diuretic and natural antioxidant. In particular, the dandelion extract may derive from the root of the dandelion, especially the species *Taraxacum officinale*.

In general, these herbs are a good source of flavinoids that can strengthen blood vessels, act as antioxidants, and have many other benefits.

A further preferred component is a burdock seed extract (*Arctium lappa*) and/or a burdock root extract (*Arctium lappa*). These extracts may act as diuretics.

A further preferred extract is a ginger extract (*Zingiber officinalis*). Ginger can act as a stimulant and carminative.

A further preferred extract is a dong quai extract (e.g. root of *Angelica sinensis*). This extract acts as a hormonal regulator.

A further preferred extract is a plantain seed extract (*Plantago major*), and/or a plantain plant extract (*Plantago major*). These extracts are detoxifiers.

A highly preferred composition (for any end use described herein in particular cellulite treatment) contains all of a plant extract from the genus *taraxacum* (dandelion), a burdock seed extract (*Arctium lappa*), a burdock root extract (*Arctium lappa*), a ginger extract (*Zingiber officinalis*), a dong quai extract (e.g. root of *Angelica sinensis*), a plantain seed extract (*Plantago major*), and a plantain plant extract (*Plantago major*).

The amount of each additional component (called herb component herein) in the composition of the invention can also be varied but typically amounts are around 25 to 100 mg of herb per dosage form. Overall, herb consumption may be around 1000 mg to 1500 mg per day.

The ratio of herbs (total) to glucans (total) is preferably in the range 1:1 to 10:1, more preferably 1.5:1 to 5:1, especially 2:1 to 4:1.

The composition of the invention may also comprise a source of inulin and/or fructooligosaccharides. The inulin and/or fructooligosaccharide are believed to act on the disaccharidase enzyme which enables "fast" sugars (e.g. glucose) to pass through the intestinal wall thereby slowing down or preventing intestinal absorption of "fast" sugars. Nondigested sugars are eliminated from the body in the natural way Inulin and fructooligosaccharides (FOS) are natural constituents of many common foods, including plants, vegetables, fruits and cereals, e.g. dahlia, helianthus, asparagus, banana, chicory, dandelion, garlic, globe artichoke, Jerusalem artichoke, leek, onion, barley, rye, salsify and wheat. The highest concentrations, on a fresh-weight basis, of inulin and FOS are found within members of the family Compositae (chicory, dandelion, Jerusalem artichoke; also Dahlia).

Inulin and fructooligosaccharides are not hydrolysed by enzymes in the small intestine and pass through the small intestine unchanged. These are therefore considered to be non-digestible carbohydrates which form part of the dietary fiber component of the diet. These do not increase the insulin level in the blood and their direct calorific value is negligible.

Inulin and fructooligosaccharides have the added advantage that they are slightly sweet in flavour and so serve to mimic the sweetening effect of sugar. These therefore rapidly saturate sweet taste receptors on the tongue (thereby quickly reducing the yearning for sugar) while containing few calories. Inulin is also believed to suppress appetite.

Inulin, which consists of molecules which are linear chains of fructose units terminated by a glucose unit, is mainly extracted from endive root.

The amounts employed would be the same as those of the herbs above.

The compositions of the invention might also contain chlorogenic acid. The amounts employed could range from 10 to 200 mg per dosage form, e.g. 25 to 100 mg.

The compositions of the invention have been found to cause a reduction in weight even over a relatively short space of time, e.g. a month. The observed reduction in weight after 30 days of treatment will preferably be statistically significant, especially having a two-sided p value of less than 0.05. A weight loss of 1 to 3 kg per month could be expected, e.g. around 1 to 3% of body weight.

The compositions of the invention may also encourage one or more of a reduction in body fat percentage, a reduction in waist circumference, a reduction in abdominal circumference or a reduction in hip circumference, in particular a statistically significant reduction in these parameters. Viewed from another aspect therefore the invention provides Beta-1,3/1,6-glucan or a composition comprising at least one beta-1,3/1,6-glucan and optionally at least one plant extract selected from the group consisting of an extract from the genus *silybum* (e.g. blessed milk thistle (*Silybum marianum*)), an extract from golden root (*Rhodiola Rosea*), a plant extract from the genus *Cynara*, e.g. global artichoke (*Cynara scolymus*), a plant extract from the genus *Schisandra* e.g. (*Schisandra chinensis*), a plant extract from the genus *Glycyrrhiza*, e.g. licorice root (*Glycyrrhiza glabra*), a plant extract from the genus *taraxacum* (dandelion), a burdock seed extract (*Arctium lappa*), a burdock root extract (*Arctium lappa*), a ginger extract (*Zingiber officinalis*), a dong quai extract (e.g. root of *Angelica sinensis*), a plantain seed extract (*Plantago major*), and a plantain plant extract (*Plantago major*) for use in reducing body fat body fat percentage, reducing in waist circumference, reducing abdominal circumference or reducing hip circumference.

Moreover, the compositions of the invention have been found to alleviate constipation. It is believed that the combination of glucans and the particular herbal mixture employed serves to reduce constipation. This forms a further aspect of the invention which therefore provides a composition as herein before defined for use in alleviating constipation.

The compositions of the invention can be prepared as tablets, capsules or indeed any other conventional dosage form. They are preferably administered orally. Dosage forms of the invention can contain any standard excipients conventional used in the pharmaceutical or nutraceutical art. Formulation of the composition into an appropriate dosage form is readily carried out by the skilled man.

Typical excipients used include microcrystalline cellulose, dicalcium phosphate, magnesium stearate, silica, titanium dioxide, stearic acid and so on. These will typically form from 1 to 250 mg of the composition.

The compositions of the invention can be used to aid weight loss in individuals who may be slightly overweight to those that might be clinically obese. Weight loss in those individuals only slightly overweight (e.g. those with a body mass index of 25 to 30) may be regarded as essentially cosmetic. With respect to the mechanism of action of the treatment it might be that the combination of the herb mixture and the Beta-1,3/1,6-Glucan has a favourable effect on the gastrointestinal system digestively as well immunologically.

Without wishing to be limited by theory, the compositions of the invention are believed to reduce fat, water retention and inflammation in the body to achieve weight loss. The weight loss emphasis is on the abdominal area; reducing swelling, fat and water storage.

The hypothesis is that in overweight individuals the abdomen is large due to more than just fat storage in the subcutaneous tissue. It is also due the digestive organs causing the viscera to produce gas/flatulence, water, waste products, free radicals, fat and mucous which are stored around and in the organs in the abdominal region.

It is also believed that excess weight is contributed to by inflammation and swelling in the tissues especially in the abdomen. Fat storage can also be caused by hypothalamic pituitary lesions and over secretion of hydrocortisone. The composition of the invention is believed to contribute to a reduction in inflammation.

The composition of the invention may also improve the function of the liver which in turn leads to better digestion. The liver will also be able to help the body improve on its immune defense thus reducing inflammation in the body.

Some of the herbs in the preferred composition of the invention support kidney function to maximise metabolism of fat and prevent retention of water.

Some of the herbs used like licorice root, schizandra and milk thistle help in digestion and in general energy level.

It is believed that prescribed use of the composition of the invention can lead to a reduction in pains in the solar plexus region. Many overweight patients also exhibit swelling around the solar plexus which may be reduced using the composition of the invention resulting in a smaller stomach by appearance.

It is also believed that use of the composition of the invention can result in a reduction of cellulite. This forms a further aspect of the invention which provides Beta-1,3/1,6-glucan or a composition comprising at least one beta-1,3/1,6-glucan and optionally at least one plant extract selected from the group consisting of an extract from the genus *silybum* (e.g. blessed milk thistle (*Silybum marianum*)), an extract from golden root (*Rhodiola Rosea*), a plant extract from the genus *Cynara*, e.g. global artichoke (*Cynara scolymus*), a plant extract from the genus *Schisandra* e.g. (*Schisandra chinensis*), a plant extract from the genus *Glycyrrhiza*, e.g. licorice root (*Glycyrrhiza glabra*), a plant extract from the genus *taraxacum* (dandelion), a burdock seed extract (*Arctium lappa*), a burdock root extract (*Arctium lappa*), a ginger extract (*Zingiber officinalis*), a dong quai extract (e.g. root of *Angelica sinensis*), a plantain seed extract (*Plantago major*), and a plantain plant extract (*Plantago major*) for reduction, elimination or prevention of cellulite.

Viewed from another aspect the invention provides a method for reducing, eliminating or preventing cellulite comprising administering to a patient Beta-1,3/1,6-glucan or a composition comprising at least one beta-1,3/1,6-glucan and optionally at least one plant extract selected from the group consisting of an extract from the genus *silybum* (e.g. blessed milk thistle (*Silybum marianum*)), an extract from golden root (*Rhodiola Rosea*), a plant extract from the genus *Cynara*, e.g. global artichoke (*Cynara scolymus*), a plant extract from the genus *Schisandra* e.g. (*Schisandra chinensis*), a plant extract from the genus *Glycyrrhiza*, e.g. licorice root (*Glycyrrhiza glabra*), a plant extract from the genus *taraxacum* (dandelion), a burdock seed extract (*Arctium lappa*), a burdock root extract (*Arctium lappa*), a ginger extract (*Zingiber officinalis*), a dong quai extract (e.g. root of *Angelica sinensis*), a plantain seed extract (*Plantago major*), and a plantain plant extract (*Plantago major*). This method is regarded as cosmetic.

It will be appreciated that in this embodiment the glucan composition may be provided for topical application, e.g. as an ointment, cream, salve or gel. The formulation of these topical compositions is well known in the art and can be achieved using standard, excipients. The topical formulation could be applied to the cellulite affected area at regular intervals e.g. once a day or morning and night. The amounts of active component present can vary but are broadly the same as those presented in relation to the weight loss composition discussed herein.

Assessment of cellulite reduction can be made visually, e.g. by a physician. It has in particular been found that the administration of the composition of the invention increases interleukin-10 concentration but does not change insulin sensitivity. Interleukin-10 is an anti-inflammatory cytokine. Inflammation has long been associated with obesity and cellulite formation so increases in the amount of interleukin-10 may reduce both those conditions.

Other benefits of using the composition of the invention may include an increase in energy, better sleep and better digestion. The composition may also prevent water retention in the limbs and joints.

The invention will now be described with reference to the following non-limiting examples.

EXAMPLE 1

A clinical trial in Norwegian females using a preparation containing Beta-1,3/1,6-Glucan and a combination of different herbs was performed. The composition is described below. The primary outcome was decreased weight, BMI, waist, stomach and hip circumferences as well as tolerability.

The results from this placebo controlled clinical study in 28 middle age females with mild to moderate overweight (BMI$\geq$27.5 kg/m$^2$) and with a waist circumference (WC$\geq$90 cm) show during a treatment period of 30 days significant reductions in body weight, BMI, BF % as well as significant reductions of waist, abdominal and hip circumferences.

Subjects and Methods

Subjects

Female subjects with slight to moderate overweight (BMI$\geq$27.5 kg/m$^2$) were invited to participate in the study. All participants gave written informed consent before entering the study, after having received information about the study procedures. The study was conducted according to the principles of the revised Declaration of Helsinki, Good Clinical Practice and local regulation.

Participants were not using any drugs for chronic diseases or on any weight reduction treatment. No diet advice or advice with respect to exercise was given to the participants before inclusion in the study. In this short-time study we were interested to study the effect of the preparation when other factors were kept unchanged.

Study Design

The study was carried out as placebo controlled single blind study in the following way. Twelve of the participants started the study with a 30 day placebo period. They were controlled initially and then after 30 days. At conclusion of the placebo period they were switched to the active preparation for a period of 30 days. Another group of 16 participants were started at the same time on active treatment. In this way 28 participants were receiving the active treatment for a period of 30 days. All the subjects were then controlled after 30 days on active treatment.

Treatment

The investigational preparation used in this study was a food supplement in which each tablet contained the following ingredients:

125 mg Beta-1,3/1,6-Glucan extract from brewer's yeast and 5.0 mg water extracts (1:10) of each the following herbs, blessed milk thistle (*Silybum marianum*), golden root (*Rhodiola rosea*), global artichoke (*Cynara scolymus*), schisandra (*Schisandra chinensis*), licorice root (*Glycyrrhiza glabra*) and dandelion (*Taraxacum*).

The dosage was two tablets in the morning and two tablets in the evening. The tablets were taken together with food and swallowed with water. No formal dose-response studies have been carried out. The total daily dose was thus 500 mg Beta-1,3/1,6-Glucan and 1200 mg of the herb mixture. The placebo tablets used in the study contained lactose. All tablets used in this study were supplied by Med-Eq AS, Tønsberg, Norway.

Performance of the Study

Initially and after 30 days (end of the study) the body weight of the subject was registered on a balance beam medical scale to the nearest 0.1 kg. Stature was measured initially on a portable stadiometer to an accuracy of 0.5 cm with the subject barefoot, feet together and head level. Other parameters measured at each visit included waist, abdominal and hip circumferences.

Body composition was measured initially and at the end of the study. Body composition was determined with bio-impedance measurements.

Statistical Evaluation

Data given in the text and tables as means±standard deviations (SDs). Data were analyzed with SAS statistical package version 8.2 and SPSS software 13.0 for Windows. In all analyses a two-sided p value of 0.05 was considered statistically significant.

Results

The results from this study are presented in the following tables 1 and 2. As can be seen from table 1 both the body weight (BW), body mass index (BMI) and the body fat (BF %) were reduced significantly during the study period of 30 days when the subjects were taking the active preparation. For the 12 patients starting with a 30 days treatment with placebo no statistical differences were seen in any of the parameters.

The average weight reduction in this study is 1.8 kg giving a weekly weight reduction of approximately 0.5 kg. The average waist reduction is 3.8 cm, while the abdominal circumference 4 cm.

Most of the subjects participating in this study reported that their gastrointestinal functions were normalized after starting taking the active preparation. Quite a few of the participants had suffered from constipation before entering the study. After starting the study, the constipation disappeared and they had an improved gastrointestinal function during the study and felt much better in that respect.

The tolerability of the treatment was excellent and none of the participants had any problems with side-effects of the active treatment during the study period.

The results from this study indicate that the preparation used has a very favourable effect on reducing fat deposits documented through the reduction of waist circumference of 3.8 cm and similar reductions in abdominal and hip circumferences.

The reduction of body weight is also significant, and it is important to note that almost 100% of the weight loss is due to fat loss.

TABLE 1

Development of BW, BMI and BF % on placebo and active treatment SD in parentheses. Ns mean no significance.

| Group | Parameter | Baseline | After 30 days | Diff | p-value |
|---|---|---|---|---|---|
| Placebo N = 12 | BW(kg) | 78.1 | 78.0 | 0.1 | ns |
| | BMI(kg/m$^2$) | 28.0 | 28.0 | 0.0 | ns |
| | BF(%) | 39.8 | 39.8 | 0.0 | ns |
| Active N = 28 | BW(kg) | 77.1 | 75.3 | 1.8 | |
| | BMI(kg/m$^2$) | 28.1 | 27.5 | 0.6 | |
| | BF(%) | 39.4 | 37.9 | 1.5 | |

TABLE 2

Development of Waist circumference (WC), Abdominal circumference (AC) and Hip circumference (HC) on placebo and active treatment. SD in parentheses. ns means no significance.

| Group | Parameter | Baseline | After 30 days | Diff | p-value |
|---|---|---|---|---|---|
| Placebo N = 12 | WC(cm) | 91.0 | 91.0 | 0.0 | Ns |
| | AC(cm) | 96.7 | 96.8 | 0.1 | Ns |
| | HC(cm) | 100.3 | 100.2 | 0.1 | Ns |
| Active N = 28 | WC(cm) | 94.9(7.6) | 91.1(7.4) | 3.8 | P ≦ 0.01 |
| | AC(cm) | 96.5(8.2) | 92.4(7.7) | 4.1 | P ≦ 0.01 |
| | HC(cm) | 99.7(8.0) | 95.7(7.8) | 4.0 | P ≦ 0.01 |

EXAMPLE 2

Weight/Cellulite Reducing Tablet

| Ingredients | Source | E-Number | mg per tablet |
|---|---|---|---|
| Beta 1,3/1,6 Glucan | Extract from yeast (*saccharomyses cerevisiae*) | | 125 |
| Dandelion root extract | Root of *Taraxacum officinale* | | 75 |
| Burdock seed extract | Seed of *Arctium lappa* | | 62.5 |
| Burdock root extract | Root of *Arctium lappa* | | 62.5 |
| Ginger extract | Rhizome of *Zingiber officinalis* | | 25 |
| Dong Quai extract | Root of *Angelica Sinensis* | | 125 |
| Plantain seed extract | Seed of *Plantago Major* | | 50 |
| Plantain plant extract | Whole plant of *Plantago Major* | | 50 |
| Microcrystalline cellulose | | E460 | 200 |
| Dicalcium Phosphate | | E341 | 200 |

-continued

| Ingredients | Source | E-Number | mg per tablet |
|---|---|---|---|
| Magnesium stearate | | E470B | 17.5 |
| Silicon dioxide, colloidal | | E551 | 7.5 |
| White film coating materials | Titanium dioxide, HPMC and stearic acid | E171, E464 and E570 | 20 |
| Total | | | 1020 |

The invention claimed is:

1. A composition for treating obesity or reducing weight in a patient in need thereof consisting of a therapeutically effective amount of an extract of *Saccharomyces cerevisae* and a therapeutically effective amount of an extract of Silybum marianum.

2. A method of treating obesity or reducing weight in a patient in need thereof consisting of administering to the patient a composition consisting of a therapeutically effective amount of an extract of *Saccharomyces crevasae* and a therapeutically effective amount of an extract of Silybum marianum.

* * * * *

UNITED STATES PATENT AND TRADEMARK OFFICE
CERTIFICATE OF CORRECTION

PATENT NO. : 8,318,218 B2  
APPLICATION NO. : 12/995081  
DATED : November 27, 2012  
INVENTOR(S) : Mortensen et al.

Page 1 of 1

It is certified that error appears in the above-identified patent and that said Letters Patent is hereby corrected as shown below:

Title Page,
Item (73) Assignee should read: MED-EQ AS, Tonsberg (NO)

Signed and Sealed this
Twenty-ninth Day of January, 2013

David J. Kappos
*Director of the United States Patent and Trademark Office*